United States Patent [19]

Diana

[11] 4,153,719

[45] May 8, 1979

[54] AROMATIC DIKETONES

[75] Inventor: Guy D. Diana, Stephentown, N.Y.

[73] Assignee: Sterling Drug Inc., New York, N.Y.

[21] Appl. No.: 830,470

[22] Filed: Sep. 6, 1977

[51] Int. Cl.$^2$ ............................................. A61K 31/36
[52] U.S. Cl. ............................. 424/282; 260/340.5 R; 260/347.8; 260/590 C; 260/590 D; 260/651 R; 260/961; 424/285; 424/331; 560/57; 568/641; 568/637; 568/639; 568/640; 568/645; 568/647; 542/459; 562/468
[58] Field of Search .................... 260/590 D, 340.5 R; 424/282, 331

[56] References Cited

U.S. PATENT DOCUMENTS

| | | | |
|---|---|---|---|
| 3,829,475 | 8/1974 | Collins | 260/520 |
| 3,917,718 | 11/1975 | Collins | 260/613 R |
| 3,978,081 | 8/1976 | Eiden et al. | 260/340.5 R X |
| 4,082,807 | 4/1978 | Eiglmeier | 260/590 D |
| 4,125,541 | 11/1978 | Diana et al. | 260/340.5 R |

*Primary Examiner*—Ethel G. Love
*Attorney, Agent, or Firm*—Thomas L. Johnson; B. Woodrow Wyatt; William G. Webb

[57] ABSTRACT

Beta-diketones substituted by an aryl-aliphatic group in which the aliphatic chain is interrupted by a cyclic group, and useful as anti-viral agents, are prepared by interacting the appropriate aryl-aliphatic halide with an alkali metal salt of a beta-diketone.

14 Claims, No Drawings

AROMATIC DIKETONES

BACKGROUND OF THE INVENTION (a) Field of the Invention

This invention relates to novel beta-diketones substituted by an aryl-aliphatic group in which the aliphatic chain is interrupted by a cyclic group, to the preparation thereof, and to compositions and methods for the use thereof as anti-viral agents.

(b) Description of the Prior Art

J. C. Collins U.S. Pat. No. 3,917,718, issued Nov. 4, 1975, discloses compounds useful as pesticidal and anti-viral agents and having the formula

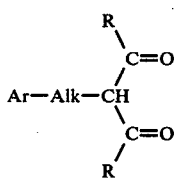

wherein Ar is phenyl or substituted phenyl, Alk is alkylene of 6-10 carbon atoms and R is lower-alkyl.

J. C. Collins and G. D. Diana U.S. Pat. No. 4,031,246, issued June 21, 1977, discloses compounds useful as pesticidal and anti-viral agents and having the formula

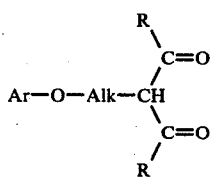

wherein Ar is phenyl or substituted phenyl, Alk is alkylene of 3-10 carbon atoms and R is lower-alkyl.

Neither of the above prior art patents shows any compounds wherein the alkylene bridge (Alk) is interrupted by a cyclic group.

SUMMARY OF THE INVENTION

In a composition of matter aspect, the invention relates to beta-diketones substituted on the carbon atom between the carbonyl groups by an aryl-aliphatic group in which the aliphatic chain is interrupted by a cyclic group. The compounds have the general formulas:

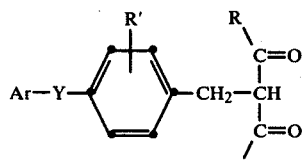

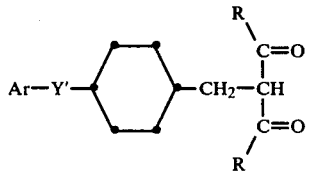

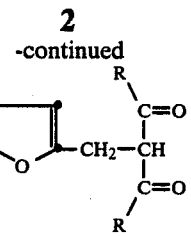

wherein:

Ar is phenyl or phenyl substituted by methylenedioxy or from one to two substituents selected from the group consisting of hydroxy, alkoxy of 1-3 carbon atoms and halogen;

Y is selected from the group consisting of $CH_2$, $CH_2CH_2$, $CH=CH$, $O$ and $OCH_2$;

Y' is selected from the group consisting of $CH_2$, $CH_2CH_2$ and $OCH_2$;

R is alkyl of 1 to 4 carbon atoms; and

R' is hydrogen or chlorine.

In a process aspect, the invention relates to a process for preparing the compounds of formulas I, II and III by reacting a compound of the formula

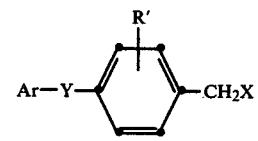

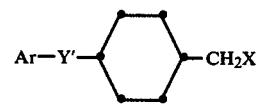

or 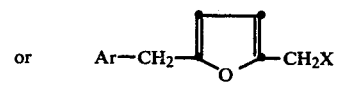

wherein X is bromine or iodine and Ar, Y, Y', R and R' have the meanings given hereinabove, with an alkali metal salt of a diketone of the formula $(RCO)_2CH_2$.

In a further composition of matter aspect, the invention relates to a composition for combatting viruses which comprises an anti-virally effective amount of a compound of formula I, II or III in admixture with a suitable carrier or diluent.

In a further process aspect, the invention relates to a method for combatting viruses which comprises contacting the locus of said viruses with an anti-virally effective amount of at least one compound of formula I, II or III.

DETAILED DESCRIPTION INCLUSIVE OF PREFERRED EMBODIMENTS

In the compounds of formulas I, II or III, when two monovalent substituents are present on the phenyl ring of Ar, the substituents can be the same or different. When halogen substituents are present, they can be any of the four common halogens, fluoro, chloro, bromo or iodo.

In the preparation of the compounds of formulas I, II and III, the reaction of the halogen intermediates of formulas IV, V and VI with an alkali metal salt of a diketone, $(RCO)_2CH_2$, takes place in an inert solvent under anhydrous conditions at ambient temperature or above (20°-100° C.). The alkali metal salt, preferably the lithium, sodium or potassium salt, can be prepared in situ in a solution of the diketone with the appropriate base, for example lithium hydride or potassium carbonate.

The intermediates of formulas IV, V and VI are prepared by standard synthetic methods. One approach is via the compounds wherein the halomethyl group (—CH₂X) is replaced by carboxy or carboalkoxy. The acid or ester is reduced by means of a metal hydride such as lithium aluminum hydride to the corresponding methanol derivative (—CH₂OH) and the latter treated with hydrogen bromide to produce the bromomethyl compound.

The compounds of formula IV where Y is CH=CH are conveniently prepared by bromination of the corresponding compounds of the formula

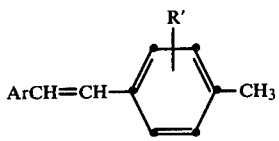

with N-bromosuccinimide.

The compounds of formulas IV or V where Y' is OCH₂ are prepared by reacting 1,4-bis(bromomethyl)-benzene or 1,4-bis-(bromomethyl)cyclohexane with a molar equivalent of a phenol, ArOH, in the presence of a base.

The compounds of formula I where Y is CH₂CH₂ can also be prepared by catalytic hydrogenation of the compounds of formula I where Y is CH=CH.

The compounds of formulas I, II or III where the Ar group is substituted by hydroxy are conveniently prepared from the corresponding compounds of formulas I, II or III where the Ar group is substituted by alkoxy by means of conventional dealkylation procedures. It is, however, possible to carry out the conversion of compounds of formulas IV, V or VI where Ar is substituted by hydroxy to compounds of formulas I, II or III, respectively, where Ar is substituted by hydroxy by reacting the former with potassium salt of a diketone, (RCO)₂CH₂, formed in situ from the diketone and potassium carbonate.

The structures of the compounds of the invention were established by the modes of synthesis, by elementary analysis, and by infrared and nuclear resonance spectral determinations.

Biological evaluation of the compounds of the invention has shown that they possess anti-viral activity. They are thus useful in combatting viruses present on inanimate surfaces as well as viral infections in animal organisms. The in vitro testing of the compounds of the invention against herpes simplex viruses types 1 and 2 and equine rhinovirus has showed that they inhibited viral growth at minimum concentrations (MIC) ranging from about 0.6 to about 50 micrograms per milliliter. The MIC values were determined by standard serial dilution procedures.

The anti-viral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams. The anti-virally effective component of the composition is present in a concentration of between about 0.6 parts per million and about 5 percent by weight, depending upon the chemical species used, the object to be treated and the type of formulation employed. For disinfection of inanimate surfaces with aqueous or aqueous-organic solutions, concentrations in the lower part of the range are effective. For topical application in medical or veterinary use in the form of ointment, cream, jelly or aerosol, concentrations in the upper part of the range are preferred.

The following examples will further illustrate the invention.

EXAMPLE 1

(a) Ethyl 4-(4-methoxybenzoyl)benzoate

A mixture of 120 g. of 4-(4-methoxybenzoyl)benzonitrile (m.p. 131°-132° C., Swiss Pat. No. 475,242), 750 ml. of 10N hydrochloric acid in ethanol, and 750 ml. of ethanol was heated under reflux for 5.5 hours. The ethanol was removed from the reaction mixture and the residue partitioned between water and ethyl acetate. The organic layer was dried over anhydrous magnesium sulfate and the solvent removed to give 130 g. of semi-solid product. The ethyl 4-(4-methoxybenzoyl)-benzoate thus obtained had m.p. 74°-81° C. when recrystallized from ethanol.

(b) Ethyl 4-(4-methoxybenzyl)benzoate

A solution of 130 g. of ethyl 4-(4-methoxybenzoyl)-benzoate in 1100 ml. of ethanol was hydrogenated in the presence of 10 g. of 10% palladium-on-carbon catalyst at 60° C. and 45 psi initial pressure. The catalyst was filtered off and the solvent removed to give 120 g. of ethyl 4-(4-methoxybenzyl)benzoate as an oil.

(c) 4-(4-Methoxybenzyl)benzoic acid

A mixture of 120 g. of ethyl 4-(4-methoxybenzyl)benzoate, 500 ml. of 2N sodium hydroxide solution and 250 ml. of ethanol was heated at reflux for two hours. The reaction mixture was cooled, diluted with water and extracted with ether. The aqueous layer was acidified with hydrochloric acid and the precipitate which formed was collected and dried to give 100 g. of 4-(4-methoxybenzyl)benzoic acid, m.p. 152°-153° C. when recrystallized from aqueous ethanol.

(d) 4-(4-Methoxybenzyl)benzyl alcohol

A solution of 110 ml. (0.11 m) of 1M boron hydride (BH₃) in tetrahydrofuran was slowly added to a solution of 24.2 g. (0.10 m) of 4-(4-methoxybenzyl)benzoic acid in 110 ml. of tetrahydrofuran at 0° C. The addition was complete in 20 minutes and the reaction mixture was stirred at room temperature for one hour. The reaction mixture was carefully acidified with hydrochloric acid and the solvent removed. The residue was partitioned between water and ether, and the ether layer was washed with aqueous sodium hydroxide, dried over anhydrous magnesium sulfate and concentrated to give 22.2 g. of 4-(4-methoxybenzyl)benzyl alcohol, m.p. 68°-72° C. when recrystallized from cyclohexane.

(e) 4-(4-Methoxybenzyl)benzyl bromide

Hydrogen bromide was bubbled through a solution of 22.2 g. of 4-(4-methoxybenzyl)benzyl alcohol in 100 ml. of benzene held at 20°–30° C. for a period of 20 minutes. The reaction mixture was washed with aqueous sodium chloride solution, then with 2N aqueous sodium hydroxide solution, dried over anhydrous magnesium sulfate and concentrated to give 27.5 g. of 4-(4-methoxybenzyl)benzyl bromide as an oil.

(f) 4-[4-(4-Methoxybenzyl)benzyl]heptane-3,5-dione [I; Ar is 4-$CH_3OC_6H_4$, Y is $CH_2$, R is $C_2H_5$, R' is H]

A mixture of 27.5 g. (0.095 m) of 4-(4-methoxybenzyl)-benzyl bromide and 20 g. (0.15 m) of the lithium salt of heptane-3,5-dione in 300 ml. of dimethylformamide was stirred at 60° C. for 2.5 days. The solvent was removed from the reaction mixture and the residue partitioned between water and ether. The ether layer was washed with water, dried over anhydrous magnesium sulfate and concentrated. The residual oil was distilled to give 20.3 g. of 4-[4-(4-methoxybenzyl)benzyl]-heptane-3,5-dione, yellow oil, b.p. 193°–199° C. (0.04 mm).

4-[4-(4-Methoxybenzyl)benzyl]heptane-3,5-dione when tested in vitro against equine rhinovirus showed anti-viral activity at a minimal inhibitory concentration (MIC) of 6 micro-grams per milliliter.

By replacing the lithium salt of heptane-3,5-dione in the foregoing preparation by a molar equivalent amount of the lithium salt of pentane-2,4-dione, nonane-4,6-dione, undecane-5,7-dione, or 1,1,7,7-tetramethylheptane-3,5-dione, it is contemplated that there can be obtained, respectively, 3-[4-(4-methoxybenzyl)benzyl]-pentane-2,4-dione [I; Ar is 4-$CH_3OC_6H_4$, Y is $CH_2$, R is $CH_3$, R' is H]; 5-[4-(4-methoxybenzyl)benzyl]nonane-4,6-dione [I; Ar is 4-$CH_3OC_6H_4$, Y is $CH_2$, R is $CH_2CH_2CH_3$, R' is H]; 6-[4-(4-methoxybenzyl)benzyl]undecane-5,7-dione [I; Ar is 4-$CH_3OC_6H_4$, Y is $CH_2$, R is $(CH_2)_3CH_3$, R' is H]; or 4-[4-(4-methoxybenzyl)benzyl]-1,1,7,7-tetramethylheptane-3,5-dione [I; Ar is 4-$CH_3OC_6H_4$, Y is $CH_2$, R is $C(CH_3)_3$, R' is H].

By replacing the 4-(4-methoxybenzoyl)benzonitrile in Example 1, part (a) above by a molar equivalent amount of 4-benzoylbenzonitrile, 4-(3,4-methylenedioxybenzoyl)benzonitrile, 4-(4-chlorobenzoyl)benzonitrile, 4-(2-chloro-4-methoxybenzoyl)-benzonitrile, 4-(4-bromobenzoyl)benzonitrile, or 4-(4-iodobenzoyl)benzonitrile, and carrying out the transformation of Example 1, parts (a) through (f), it is contemplated that there can be obtained, respectively, 4-(4-benzylbenzyl)heptane-3,5-dione [I; Ar is $C_6H_5$, Y is $CH_2$, R is $C_2H_5$, R' is H]; 4-[4-(3,4-methylenedioxybenzyl)benzyl]heptane-3,5-dione [I; Ar is 3,4-$CH_2O_2C_6H_3$, Y is $CH_2$, R is $C_2H_5$, R' is H]; 4-[4-(4-chlorobenzyl)benzyl]heptane-3,5-dione [I; Ar is 4-$ClC_6H_4$, Y is $CH_2$, R is $C_2H_5$, R' is H]; 4-[4-(2-chloro-4-methoxybenzyl)benzyl]-heptane-3,5-dione [I; Ar is 2-Cl-4-$CH_3OC_6H_3$, Y is $CH_2$, R is $C_2H_5$, R' is H]; 4-[4-(4-bromobenzyl)benzyl]heptane-3,5-dione [I; Ar is 4-$BrC_6H_4$, Y is $CH_2$, R is $C_2H_5$, R' is H]; or 4-[4-(4-iodobenzyl)-benzyl]heptane-3,5-dione [I; Ar is 4-$IC_6H_4$, Y is $CH_2$, R is $C_2H_5$, R' is H].

The intermediate benzonitriles, $ArCOC_6H_4CN$, are readily prepared by a Friedel-Crafts type reaction between p-bromobenzoyl chloride and ArH, followed by reaction of the resulting benzophenone derivative $ArCOC_6H_4Br$ with cuprous cyanide to replace the bromine atom by a cyano group.

The transformation of Example 1(f) can alternatively be effected by heating 4-(4-methoxybenzyl)benzyl bromide with heptane-3,5-dione in the presence of potassium carbonate and potassium iodide in an inert solvent such as 2-butanone.

EXAMPLE 2

4-[4-(4-Hydroxybenzyl)benzyl]heptane-3,5-dione [I; Ar is 4-$HOC_6H_4$, Y is $CH_2$, R is $C_2H_5$, R' is H]

A solution of 29.15 g. (0.116 m, 11 ml.) of boron tribromide in 160 ml. of methylene dichloride was added dropwise to a stirred solution of 26 g. (0.077 m) of 4-[4-(4-methoxybenzyl)benzyl]heptane-3,5-dione (Example 1) in 160 ml. of methylene dichloride held at −65° C. The reaction mixture was stirred for three hours at room temperature, 500 ml. of ice-water then added and the stirring continued for 30 minutes. The organic layer was washed with saturated sodium carbonate solution, dried over anhydrous magnesium sulfate and concentrated. The residue was partitioned between water and ether with a trace of hydrochloric acid added. The mixture was shaken for 30 minutes and the ether layer separated and washed with sodium bicarbonate solution. The 22 g. of oil obtained after removal of the ether was chromatographed on 1 kg. of silica, packed wet with ethyl acetate:hexane 1:4 and eluted with the same solvent, taking 500 ml. fractions. Fractions 7–15 gave 17.5 g. of 4-[4-(4-hydroxybenzyl)benzyl]heptane-3,5-dione, which was recrystallized from hexane-ether to give 6.5 g. of colorless plates, m.p. 65°–66° C.; MIC = 3 microg/ml (equine rhinovirus).

Alternatively, the compound of Example 2 can be prepared by demethylation of 4-(4-methoxybenzyl)benzyl bromide (Example 1e) with boron tribromide according to the procedure of Example 2, and heating the resulting 4-(4-hydroxybenzyl)benzyl bromide with heptane-3,5-dione in the presence of potassium carbonate and potassium iodide in an inert solvent such as 2-butanone.

EXAMPLE 3

(a) 4-Benzylbenzyl bromide was prepared from 20 g. of 4-benzylbenzyl alcohol [Maquin et al., Compt. rend. 234, 629-31, 1952] and hydrogen bromide according to the procedure of Example 1, part (e). An oil (25.7 g.) was obtained which was used directly in the next reaction.

(b) 4-(4-Benzylbenzyl)heptane-3,5-dione [I; Ar is $C_6H_5$, Y is $CH_2$, R is $C_2H_5$, R' is H] was prepared from 25.7 g. of 4-benzylbenzyl bromide and 20 g. of the lithium salt of heptane-3,5-dione according to the procedure of Example 1, part f. There was obtained 18.1 g. of product, light yellow oil, b.p. 160° C. (0.04 mm); MIC = 6 microg/ml (equine rhinovirus).

EXAMPLE 4

(a) 4-(4-Methoxyphenoxy)benzyl alcohol was prepared from 10.5 g. of 4-(4-methoxyphenoxy)benzoic acid [Langham et al., J. Am. Chem. Soc. 63, 545-9 (1941)] and 60 ml. of 1M boron hydride ($BH_3$) in tetrahydrofuran according to the procedure of Example 1, part (d), affording 9.4 g. of solid used directly in the next reaction.

(b) 4-(4-Methoxyphenoxy)benzyl bromide was prepared from 9.4 g. of 4-(4-methoxyphenoxy)benzyl alcohol and hydrogen bromide according to the procedure of Example 1, part (d), affording 11.2 g. of oil used directly in the next reaction.

(c) 4-[4-(4-Methoxyphenoxy)benzyl]heptane-3,5-dione [I; Ar is 4-CH$_3$OC$_6$H$_4$, Y is O, R is C$_2$H$_5$, R' is H] was prepared from 11.2 g. of 4-(4-methoxyphenoxy)-benzyl bromide and 8 g. of the lithium salt of heptane-3,5-dione in 100 ml. of dimethylformamide, heating at 90° C. for about 15 hours. There was obtained 7.6 g. of product as a pale yellow oil, b.p. 182°–186° C. (0.05 mm); MIC = 3 microg/ml (equine rhinovirus).

EXAMPLE 5

(a) Ethyl 4-(4-methoxystyryl)benzoate

4'-Methoxystilbenenitrile, 72.5 g. [Neher et al., Helv. Chim. Acta 29, 449-67 (1946)] in 1 liter of 5N hydrogen chloride in ethanol was heated under reflux for eight hours. An additional 100 ml. of 10N hydrogen chloride in ethanol was added and refluxing continued for about sixteen hours. An additional 100 ml. of 10N hydrogen chloride in ethanol was then added and refluxing continued for six hours. The reaction mixture was diluted with 2 liters of water, and the solid product which separated was collected by filtration and air-dried. The product was dissolved in methylene dichloride, dried over anhydrous magnesium sulfate and the solvent removed to give 73 g. of ethyl 4-(4-methoxystyryl)benzoate, m.p. 191°–192° C. when recrystallized from ethanol.

(b) 4-(4-Methoxystyryl)benzyl alcohol

Ethyl 4-(4-methoxystyryl)benzoate (67 g.) in 600 ml. of tetrahydrofuran was gradually added to a suspension of 12 g. of lithium aluminum hydride in 300 ml. of tetrahydrofuran at such a rate to maintain gentle reflux. The reaction mixture was heated at reflux for two hours, then cooled and 24 ml. of water in 24 ml. of tetrahydrofuran added slowly. The mixture was stirred for one hour, heated to reflux temperature and filtered hot through a steam-jacketed funnel. The solvent was removed from the filtrate to give 55 g. of 4-(4-methoxystyryl)benzyl alcohol, m.p. 200°–202° C. when recrystallized from ethanol.

(c) 4-(4-Methoxystyryl)benzyl bromide was prepared from 55 g. of 4-(4-methoxystyryl)benzyl alcohol and hydrogen bromide in 750 ml. of methylene dichloride according to the procedure of Example 1, part (e); yield 50 g., m.p. 147°–148° C. when recrystallized from ethyl acetate.

(d) 4-[4-(4-Methoxystyryl)benzyl]heptane-3,5-dione [I; Ar is 4-CH$_3$OC$_6$H$_4$, Y is CH=CH, R is C$_2$H$_5$, R' is H] was prepared from 50 g. of 4-(4-methoxystyryl)benzyl bromide and 35 g. of the lithium salt of heptane-3,5-dione in 500 ml. of dimethylformamide according to the procedure of Example 1, part (f); yield 60 g., pale yellow solid, m.p. 105°–107° C. when recrystallized from ether. The ultraviolet spectrum showed the compound to be the trans-isomer.

4-[4-(4-Methoxystyryl)benzyl]heptane-3,5-dione when tested in vitro against equine rhinovirus or herpes virus type 1 showed anti-viral activity at minimum inhibitory concentrations (MIC) of less than 0.6 and 0.7 micrograms per milliliter, respectively. It also was found to reduce by 95 percent the virus titer of an equine rhinovirus culture on rhesus monkey trachea tissue.

EXAMPLE 6

4-[4-(4-Methoxyphenethyl)benzyl]heptane-3,5-dione [I; Ar is CH$_3$OC$_6$H$_4$, Y is CH$_2$CH$_2$, R is C$_2$H$_5$, R' is H]

A solution of 25 g. of 4-[4-(4-methoxystyryl)benzyl]-heptane-3,5-dione (Example 5d) in 175 ml. of ethyl acetate was hydrogenated in the presence of 2.5 g. of palladium-on-carbon catalyst. The catalyst was removed by filtration, the solvent removed and the residual oil (23.5 g.) distilled to give 7 g. of 4-[4-(4-methoxyphenethyl)benzyl]heptane-3,5-dione as a colorless liquid, b.p. 190°–196° C. (0.08 mm); MIC = 3 microg/ml. (equine rhinovirus).

EXAMPLE 7

4-[4-(4-Hydroxystyryl)benzyl]heptane-3,5-dione [I; Ar is 4-HOC$_6$H$_4$, Y is CH=CH, R is C$_2$H$_5$, R' is H] was prepared from 14.8 g. of 4-[4-(4-methoxystyryl)benzyl]-heptane-3,5-dione (Example 5d) and boron tribromide in methylene dichloride according to the procedure of Example 2. The crude product was triturated with hot methanol and recrystallized from acetonitrile to give 2.7 g. of 4-[4-(4-hydroxystyryl)benzyl]heptane-3,5-dione, trans-isomer, m.p. 166°–167° C.: MIC = 1.5 microg/ml. (herpes 2).

EXAMPLE 8

(a) 4-(4-Chlorostyryl)benzyl bromide

A mixture of 5.7 g. (0.025 m) of 4-chloro-4'-methyl-stilbene (m.p. 196°–197° C.) and 4.43 g. (0.025 m) of N-bromosuccinimide in 124 ml. of carbon tetrachloride was heated at reflux for eight hours. The reaction mixture was filtered hot, allowed to cool and stand overnight and again filtered to remove a small amount of amorphous material. The solvent was removed in vacuo and the residue crystallized from cyclohexane to give 4-(4-chlorostyryl)benzyl bromide, m.p. 130°–132° C. in 85% yield.

(b) 4-[4-(4-Chlorostyryl)benzyl]heptane-3,5-dione [I; Ar is 4-ClC$_6$H$_4$, Y is CH=CH, R is C$_2$H$_5$, R' is H]

A solution of 6.4 g. (0.05 m) of heptane-3,5-dione in 10 ml. of dimethylformamide was added dropwise during 15 minutes to a suspension of 0.4 g. (0.05 m) of lithium hydride in 40 ml. of dimethylformamide. To this mixture was added 13.2 g. (0.043 m) of 4-(4-chlorostyryl)benzyl bromide, and the reaction mixture was stirred at 40° C. for four hours and then poured into 500 ml. of cold water. The solid product was collected and recrystallized successively from ethanol, cyclohexane and acetonitrile to give 6.1 g. of 4-[4-(4-chlorostyryl)-benzyl]heptane-3,5-dione, colorless flakes, m.p. 132°–133° C.

By replacing the 4-chloro-4'-methylstilbene in Example 8, part (a) by a molar equivalent amount of 4-fluoro-4'-methylstilbene, 4-bromo-4'-methylstilbene or 4-iodo-4'-methylstilbene, and carrying out the transformations of Example 8, parts (a) and (b), it is contemplated that there can be obtained, respectively, 4-[4-(4-fluorostyryl)benzyl]heptane-3,5-dione [I; Ar is 4-FC$_6$H$_4$, Y is CH=CH, R is C$_2$H$_5$, R' is H]; 4-[4-(4-bromostyryl)benzyl]heptane-3,5-dione [I; Ar is 4-BrC$_6$H$_4$, Y is CH=CH, R is C$_2$H$_5$, R' is H]; or 4-[4-(4-iodostyryl)benzyl]heptane-3,5-dione [I; Ar is 4-IC$_6$H$_4$, Y is CH=CH, R is C$_2$H$_5$, R' is H].

EXAMPLE 9

(a) 4-Styrylbenzyl bromide was prepared from 35.4 g. of 4-methylstilbene and 35.6 g. of N-bromosuccinimide in carbon tetrachloride according to the procedure of Example 8(a); yield 35.5 g., m.p. 125°-127° C. after recrystallization from benzene-cyclohexane and acetonitrile.

(b) 4-(4-Styrylbenzyl)heptane-3,5-dione [I; Ar is $C_6H_5$, Y is CH=CH, R is $C_2H_5$, R' is H] was prepared from 38.5 g. of 4-styrylbenzyl bromide, 25.6 g. of heptane-3,5-dione and 1.6 g. of lithium hydride, according to the procedure of Example 8, part (b); yield 10.1 g. trans-isomer, m.p. 106°-107° C. after recrystallization from acetonitrile and then from methanol.

EXAMPLE 10

(a) 2-Chloro-4-methoxy-4'-methylstilbene

A mixture of 62.5 g. (0.4 m) of 2-chloro-4-methoxyaniline, 120 ml. of concentrated hydrochloric acid and 20 ml. of water was heated to boiling and then cooled in ice. There was then added 120 g. of ice followed by a solution of 28 g. (0.4 m) of sodium nitrite in 60 ml. of water over a 15 minute period. This mixture was stirred for 15 minutes, filtered, and 88 g. of sodium acetate was added. The resulting solution of diazotized compound was added to a stirred suspension of 65 g. (0.4 m) of 4-methylcinnamic acid in 1200 ml. of acetone. Cupric chloride (20 g.) was then added, and the reaction mixture was stirred for three hours and allowed to stand for 2.5 days. The reaction mixture was diluted with water, and the solid product collected and recrystallized from toluene to give 35.2 g. of 2-chloro-4-methoxy-4'-methylstilbene, m.p. 144°-145° C.

(b) 4-(2-Chloro-4-methoxystyryl)benzyl bromide

A mixture of 35.2 g. (0.136 m) of 2-chloro-4-methoxy-4'-methylstilbene, 30.0 g. (0.158 m) of N-bromosuccinimide, 0.5 g. of benzoyl peroxide and 600 ml. of carbon tetrachloride was heated at reflux for five hours. The reaction mixture was kept overnight at room temperature, then filtered and the solvent removed in vacuo. The residue was crystallized from ether and then recrystallized from a methyl isobutyl ketone-ether mixture to give 26.0 g. of 4-(2-chloro-4-methoxystyryl)benzyl bromide, m.p. 99°-100° C.

(c) 4-[4-(2-Chloro-4-methoxystyryl)benzyl]heptane-3,5-dione [I; Ar is 2-Cl-4-$CH_3OC_6H_3$, Y is CH=CH, R is $C_2H_5$, R' is H] was prepared from 28.3 g. of 4-(2-chloro-4-methoxystyryl)benzyl bromide, 12.8 g. of heptane-3,5-dione and 0.8 g. of lithium hydride, according to the procedure of Example 8, part (b); yield 14.6 g. trans-isomer, yellow crystals, m.p. 93°-95° C. after recrystallization from methanol; MIC = 1.5 microg/ml. (herpes 2).

EXAMPLE 11

4-[4-(2-Chloro-4-hydroxystyryl)benzyl]heptane-3,5-dione [I; Ar is 2-Cl-4-$HOC_6H_3$, Y is CH=CH, R is $C_2H_5$, R' is H] was prepared from 16.8 g. of 4-[4-(2-chloro-4-methoxystyryl)benzyl]heptane-3,5-dione (Example 10c) and 32.8 g. of boron tribromide in methylene dichloride according to the procedure of Example 2; yield 4.8 g. trans-isomer, pale yellow-white crystals, m.p. 124°-125° C. after repeated recrystallization from methanol; MIC = 1.5 microg/ml. (herpes 2).

EXAMPLE 12

(a) 2-Chloro-4-methoxybenzyldiethylphosphonate

A mixture of 67.0 g. (0.286 m) of 2-chloro-4-methoxybenzyl bromide and 50.0 g. (0.3 m) of triethyl phosphite was heated at reflux while allowing ethyl bromide to distil out at 120°-130° C. for one hour. The product was distilled, collecting the fraction boiling at 140°-149° C. (0.3 mm), used directly in the next reaction.

(b) 2,3'-Dichloro-4-methoxy-4'-methylstilbene

To a suspension of 7.4 g. (0.154 m) of 50% sodium hydride in 180 ml. of dimethylformamide was added 6.5 ml. of absolute methanol followed by 45.1 g. (0.154 m) of 2-chloro-4-methoxybenzyldiethylphosphonate. The mixture was cooled to 7° C. and 23.7 g. (0.154 m) of 3-chloro-4-methylbenzaldehyde in 20 ml. of dimethylformamide was added in portions. The reaction mixture was stirred 15 minutes at room temperature and poured into 1 liter of water. The solid product was collected and partitioned between water and methylene dichloride. The organic layer was separated, dried over anhydrous magnesium sulfate and concentrated in vacuo. The residue was recrystallized successively from ethanol, ethanol-acetonitrile and cyclohexane-n-hexane to give 27.8 g. of 2,3'-dichloro-4-methoxy-4'-methylstilbene, m.p. 77°-79° C.

(c) 4-(2-Chloro-4-methoxystyryl)-2-chlorobenzyl bromide was prepared from 27.8 g. of 2,3'-dichloro-4-methoxy-4'-methylstilbene, 17.8 g. of N-bromosuccinimide and 0.5 g. of benzoyl peroxide in carbon tetrachloride according to the procedure of Example 10(b); yield 23.0 g., m.p. 106°-108° C.

(d) 4-[4-(2-Chloro-4-methoxystyryl)-2-chlorobenzyl]heptane-3,5-dione [I; Ar is 2-Cl-4-$CH_3OC_6H_3$, Y is CH=CH, R is $C_2H_5$, R' is 2Cl] was prepared from 23.0 g. of 4-(2-chloro-4-methoxystyryl)-2-chlorobenzyl bromide, 15.9 g. of heptane-3,5-dione and 0.8 g. of lithium hydride, according to the procedure of Example 8, part (b); yield 16.7 g. trans-isomer, pale yellow crystals, m.p. 89°-90° C. after recrystallization from methanol-ether and from isopropyl acetate; MIC = 1.5 microg/ml. (herpes 2).

EXAMPLE 13

(a) 1-Bromomethyl-4-(2-chloro-4-methoxyphenoxymethyl)cyclohexane

A mixture of 23.8 g. (0.15 m) of 2-chloro-4-methoxyphenol, 162.0 g. (0.60 m) of 1,4-bis(bromomethyl)cyclohexane, 62.1 g. of potassium carbonate, 3.0 g. of potassium iodide and 1000 ml. of 2-butanone was heated at reflux for 24 hours. The solvent was removed in vacuo and the residue partitioned between water and methylene dichloride. The organic layer was dried and concentrated, and the residue distilled at 163°-165° C. (0.005 mm) to give 33.8 g. of product which crystallized. The latter was recrystallized from ether to give 20.8 g. of 1-bromomethyl-4-(2-chloro-4-methoxyphenoxymethyl)cyclohexane, trans-isomer, m.p. 74°-78° C.

By replacing the 1,4-bis(bromomethyl)cyclohexane in the foregoing preparation by a molar equivalent amount of 1,4-bis(bromomethyl)benzene, it is contemplated that 4-(2-chloro-4-methoxyphenoxymethyl)benzyl bromide can be prepared.

(b) 4-[1-(2-Chloro-4-methoxyphenoxymethyl)-4-(cyclohexylmethyl)]heptane-3,5-dione [II; Ar is 2-Cl-4-CH$_3$OC$_6$H$_3$, Y' is OCH$_2$, R is C$_2$H$_5$]

A mixture of 19.2 g. (0.055 m) of 1-bromomethyl-4-(2-chloro-4-methoxyphenoxymethyl)cyclohexane, 16.3 g. (0.127 m) of 3,5-heptanedione, 4.6 g. of potassium iodide, 16.0 g. of potassium carbonate and 200 ml. of 2-butanone was heated at reflux for 43 hours. The reaction mixture was concentrated to remove the solvent and added to 480 ml. of ice-water containing 20 ml. of concentrated hydrochloric acid. The aqueous mixture was extracted with ether and the ether layer washed with saturated sodium chloride solution, dried over anhydrous magnesium sulfate and concentrated in vacuo. The residue was distilled to remove excess diketone and the remaining material recrystallized successively from pentane, heptane and cyclohexane-ethanol to give 5.3 g. of 4-[1-(2-chloro-4-methoxyphenoxymethyl)-4-(cyclohexylmethyl)]heptane-3,5-dione, trans-isomer, m.p. 60°–62° C.; MIC = 6 microg/ml. (herpes 2).

By replacing the 1-bromomethyl-4-(2-chloro-4-methoxyphenoxymethyl)cyclohexane in the foregoing preparation by a molar equivalent amount of 4-(2-chloro-4-methoxyphenoxymethyl)benzyl bromide, it is contemplated that 4-[4-(2-chloro-4-methoxyphenoxymethyl)benzyl]heptane-3,5-dione [I; Ar is 2-Cl-4-CH$_3$OC$_6$H$_3$, Y is OCH$_2$, R is C$_2$H$_5$, R' is H] can be prepared.

EXAMPLE 14

(a) 4-(4-Methoxybenzyl)cyclohexanecarboxylic acid

A solution of 49.5 g. of 4-(4-methoxybenzyl)benzoic acid (Example 1c) in 1000 ml. of isoamyl alcohol was heated at reflux and 109 g. of sodium was added in pieces over a 40 minute period. The reaction mixture was heated under reflux for three hours, then cooled and steam distilled until 2.5 liters of distillate was obtained. The resulting aqueous solution was acidified with concentrated hydrochloric acid and extracted with ether. The ether extracts were dried over anhydrous magnesium sulfate and the solvent removed to give 34 g. of a crystalline residue comprising a mixture of the desired compound with the corresponding cyclohex-1-enecarboxylic acid. The latter mixture was dissolved in 170 ml. of ethanol and hydrogenated in the presence of 3 g. of 10% palladium-on-carbon catalyst. The catalyst was filtered off and the solvent removed to give 34 g. of 4-(4-methoxybenzyl)cyclohexanecarboxylic acid, used directly in the next reaction without further purification.

(b) 4-(4-Methoxybenzyl)cyclohexanemethanol was prepared by reduction of 34 g. of 4-(4-methoxybenzyl)cyclohexanecarboxylic acid with 180 ml. of 1M boron hydride (BH$_3$) in tetrahydrofuran according to the procedure of Example 1, part (d). The product was distilled to give 25.4 g. of 4-(4-methoxybenzyl)cyclohexanemethanol, b.p. 132°–136° C. (0.03 mm).

(c) 4-(4-Methoxybenzyl)cyclohexylmethyl bromide

Phosphorus tribromide (10 g., 0.37 m) was added dropwise over 30 minutes to a stirred solution of 23.4 g. (0.10 m) of 4-(4-methoxybenzyl)cyclohexanemethanol in 75 ml. of benzene, cooled in an ice bath. The reaction mixture was stirred at 0° C. for 1.5 hours and then at room temperature for 2.5 days. Ether (100 ml.) and 50 ml. of water were added, followed by 50 ml. of 2N sodium hydroxide solution, added slowly with cooling. The mixture was extracted with ether and the ether dried over anhydrous magnesium sulfate and concentrated to give 22 g. of oil which was distilled to give 17.5 g. of 4-(4-methoxybenzyl)cyclohexylmethyl bromide, b.p. 126°–128° C. (0.03 mm).

(d) 4-(4-Methoxybenzyl)cyclohexylmethyl iodide

A mixture of 17.5 g. (0.065 m) of 4-(4-methoxybenzyl)cyclohexylmethyl bromide, 11 g. (0.073 m) of sodium iodide and 100 ml. of acetone was heated under reflux for two hours. The solvent was removed, the residue partitioned between water and ether, and the ether layer dried and concentrated to give 19.8 g. of oil, used directly in the next reaction.

(e) 4-[4-(4-Methoxybenzyl)cyclohexylmethyl]heptane-3,5-dione [II; Ar is 4-CH$_3$OC$_6$H$_4$, Y' is CH$_2$, R is C$_2$H$_5$]

A mixture of 19.8 g. of 4-(4-methoxybenzyl)cyclohexylmethyl iodide, 13 g. of the lithium salt of heptane-3,5-dione and 150 ml. of dimethylformamide was heated to 60°–80° C. for 2 days. The solvent was removed from the reaction mixture and the residue partitioned between water and ether. The ether layer was dried over anhydrous magnesium sulfate and concentrated. The residual oil was distilled to give 12.7 g. of 4-[4-(4-methoxybenzyl)cyclohexylmethyl]heptane-3,5-dione, colorless liquid, b.p. 182°–186° C. (0.02 mm); MIC = 6 microg/ml. (equine rhinovirus).

By replacing the lithium salt of heptane-3,5-dione in the foregoing preparation by a molar equivalent amount of the lithium salt of pentane-2,4-dione, nonane-4,6-dione, undecane-5,7-dione, or 1,1,7,7-tetramethylheptane-3,5-dione, it is contemplated that there can be obtained, respectively, 3-[4-(4-methoxybenzyl)cyclohexylmethyl]pentane-2,4-dione [II; Ar is 4-CH$_3$OC$_6$H$_4$, Y' is CH$_2$, R is CH$_3$]; 5-[4-(4-methoxybenzyl)cyclohexylmethyl]nonane-4,6-dione [II; Ar is 4-CH$_3$OC$_6$H$_4$, Y' is CH$_2$, R is CH$_2$CH$_2$CH$_3$]; 6-[4-(4-methoxybenzyl)cyclohexylmethyl]undecane-5,7-dione [II; Ar is 4-CH$_3$OC$_6$H$_4$, Y' is CH$_2$, R is (CH$_2$)$_3$CH$_3$]; or 4-[4-(4-methoxybenzyl)cyclohexylmethyl]-1,1,7,7-tetramethylheptane-3,5-dione [II; Ar is 4-CH$_3$OC$_6$H$_4$, Y' is CH$_2$, R is C(CH$_3$)$_3$].

By replacing the 4-(4-methoxybenzyl)benzoic acid starting material in Example 14, part (a), by a molar equivalent amount of 4-benzylbenzoic acid, 4-(3,4-methylenedioxybenzyl)benzoic benzoic acid, 4-(4-chlorobenzyl)benzoic acid, 4-(4-bromobenzyl)benzoic acid, or 4-(2-chloro-4-methoxybenzyl)benzoic acid, and carrying out the transformations of Example 14, parts (a) through (e), it is contemplated that there can be prepared, respectively, 4-(4-benzylcyclohexylmethyl)heptane-3,5-dione [II; Ar is C$_6$H$_5$, Y' is CH$_2$, R is C$_2$H$_5$]; 4-[4-(3,4-methylenedioxybenzyl)cyclohexylmethyl]heptane-3,5-dione [II; Ar is 3,4-CH$_2$O$_2$C$_6$H$_3$, Y' is CH$_2$, R is C$_2$H$_5$]; 4-[4-(4-chlorobenzyl)cyclohexylmethyl]heptane-3,5-dione [II; Ar is 4-ClC$_6$H$_4$, Y' is CH$_2$, R is C$_2$H$_5$]; 4-[4-(4-bromobenzyl)cyclohexylmethyl]heptane-3,5-dione [II; Ar is 4-BrC$_6$H$_4$, Y' is CH$_2$, R is C$_2$H$_5$]; or 4-[4-(2-chloro-4-methoxybenzyl)cyclohexylmethyl]heptane-3,5-dione [II; Ar is 2-Cl-4-CH$_3$OC$_6$H$_3$, Y' is CH$_2$, R is C$_2$H$_5$].

It is further contemplated that 4-[4-(4-methoxybenzyl)cyclohexylmethyl]heptane-3,5-dione can be demethylated with boron tribromide according to the procedure of Example 2 to give 4-[4-(4-hydroxybenzyl)cyclohexylmethyl]heptane-3,5-dione [II; Ar is 4-HOC$_6$H$_4$, Y' is CH$_2$, R is C$_2$H$_5$].

It is further contemplated that 4-(4-methoxystyryl)-benzoic acid (obtained by hydrolysis of the ethyl ether of Example 5, part (a)) can be used as a starting material in place of 4-(4-methoxybenzyl)benzoic acid in Example 14, part (a), and carried through the succeeding transformations of Example 14, parts (a) through (f) to produce 4-[4-(4-methoxyphenethyl)cyclohexylmethyl]-heptane-3,5-dione [II; Ar is 4-CH$_3$OC$_6$H$_4$, Y' is CH$_2$CH$_2$, R is C$_2$H$_5$].

EXAMPLE 15

(a) Ethyl 5-(3,4-methylenedioxybenzyl)-2-furoate

A solution of 60 g. of 3,4-methylenedioxybenzyl bromide in 200 ml. of carbon disulfide was slowly added over a period of 45 minutes to a solution of 260 g. of ethyl 2-furoate and 20 g. of zinc chloride in 600 ml. of carbon disulfide held at −10° C. The reaction mixture was allowed to warm to room temperature, filtered, extracted with water and saturated sodium chloride solution, and dried over anhydrous sodium sulfate. The solvent was removed and the residue distilled to give 27 g. of ethyl 5-(3,4-methylenedioxybenzyl)-2-furoate, b.p. 162°-166° C. (0.5 mm), which crystallized to a solid, m.p. 67°-68° C.

(b) 5-(3,4-Methylenedioxybenzyl)furfuryl alcohol

A solution of 15.3 g. of ethyl 5-(3,4-methylenedioxybenzyl)-2-furoate in 75 ml. of tetrahydrofuran was added dropwise to a suspension of 4 g. of lithium aluminum hydride in 125 ml. of tetrahydrofuran at such a rate as to maintain reflux. The reaction mixture was then stirred for 45 minutes, and the excess lithium aluminum hydride was decomposed by dropwise addition of 50% aqueous tetrahydrofuran and stirring for 30 minutes. The mixture was filtered and the solvent removed. The residue was recrystallized from ether-pentane to give 9.8 g. of 5-(3,4-methylenedioxybenzyl)furfuryl alcohol, m.p. 68°-69° C.

(c) 5-(3,4-Methylenedioxybenzyl)furfuryl bromide

A solution of 6.6 g. of phosphorus tribromide in 50 ml. of ether was added dropwise to a solution of 15 g. of 5-(3,4-methylenedioxybenzyl)furfuryl alcohol in 150 ml. of ether held at 0° C. After the addition was completed, the mixture was stirred for one hour at room temperature and then shaken with 20 ml. of 50% aqueous sodium hydroxide for 15 minutes. The organic layer was separated, washed with water, dried over potassium hydroxide and concentrated. The resulting product was used directly in the next reaction.

(d) 4-[5-(3,4-Methylenedioxybenzyl)-2-furfuryl]heptane-3,5-dione [III; Ar is 3,4-CH$_2$O$_2$C$_6$H$_3$, R is C$_2$H$_5$]

The product of the reaction of part (c) above was dissolved in 175 ml. of dimethylformamide and 15 g. of the lithium salt of heptane-3,5-dione was added. The reaction mixture was kept at 50°-60° C. for about 16 hours. The solvent was then removed and the residue partitioned between water and ether. The ether layer was washed with water, dried and concentrated. The residue was distilled to give 13 g. of 4-[5-(3,4-methylenedioxybenzyl)-2-furfuryl]heptane-3,5-dione, yellow oil, b.p. 191°-193° C. (0.5 mm); MIC = 6 microg/ml. (equine rhinovirus).

By replacing the lithium salt of heptane-3,5-dione in the foregoing preparation by a molar equivalent amount of the lithium salt of pentane-2,4-dione, nonane-4,6-dione, undecane-5,7-dione, or 1,1,7,7-tetramethylheptane-3,5-dione, it is contemplated that there can be obtained, respectively, 3-[5-(3,4-methylenedioxybenzyl)-2-furfuryl]pentane-2,4-dione [III; Ar is 3,4-CH$_2$O$_2$C$_6$H$_3$, R is CH$_3$]; 5-[5-(3,4-methylenedioxybenzyl)-2-furfuryl]nonane-4,6-dione [III; Ar is 3,4-CH$_2$O$_2$C$_6$H$_3$, R is CH$_2$CH$_2$CH$_3$]; 6-[5-(3,4-methylenedioxybenzyl)-2-furfuryl]undecane-5,7-dione [III; Ar is 3,4-CH$_2$O$_2$C$_6$H$_3$, R is (CH$_2$)$_3$CH$_3$]; or 4-[5-(3,4-methylenedioxybenzyl)-2-furfuryl]-1,1,7,7-tetramethylheptane-3,5-dione [III; Ar is 3,4-CH$_2$O$_2$C$_6$H$_3$, R is C(CH$_3$)$_3$].

By replacing the 3,4-methylenedioxybenzyl bromide starting material in Example 15, part (a), by a molar equivalent amount of benzyl bromide, 4-chlorobenzyl bromide, 4-bromobenzyl bromide, 4-fluorobenzyl bromide, 2-chloro-4-methoxybenzyl bromide, or 4-ethoxybenzyl bromide, and carrying out the transformations of Example 15, parts (a) through (d), it is contemplated that there can be prepared, respectively, 4-(5-benzyl-2-furfuryl)heptane-3,5-dione [III; Ar is C$_6$H$_5$, R is C$_2$H$_5$]; 4-[5-(4-chlorobenzyl)-2-furfuryl]heptane-3,5-dione [III; Ar is 4-ClC$_6$H$_4$, R is C$_2$H$_5$]; 4-[5-(4-bromobenzyl)-2-furfuryl]heptane-3,5-dione [III; Ar is 4-BrC$_6$H$_4$, R is C$_2$H$_5$]; 4-[5-(4-fluorobenzyl)-2-furfuryl]heptane-3,5-dione [III; Ar is 4-FC$_6$H$_4$, R is C$_2$H$_5$]; 4-[5-(2-chloro-4-methoxybenzyl)-2-furfuryl]heptane-3,5-dione [III; Ar is 2-Cl-4-CH$_3$OC$_6$H$_3$, R is C$_2$H$_5$]; or 4-[5-(4-ethoxybenzyl)-2-furfuryl]heptane-3,5-dione [III; Ar is 4-C$_2$H$_5$OC$_6$H$_4$, R is C$_2$H$_5$].

It is further contemplated that 4-[5-(2-chloro-4-methoxybenzyl)-2-furfuryl]heptane-3,5-dione can be demethylated with boron tribromide according to the procedure of Example 2 to give 4-[5-(2-chloro-4-hydroxybenzyl)-2-furfuryl]heptane-3,5-dione [III; Ar is 2-Cl-4-HOC$_6$H$_3$, R is C$_2$H$_5$].

I claim:

1. A compound of the formula

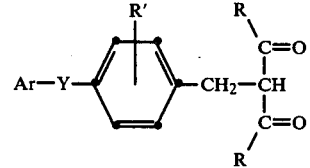

wherein:
Ar is phenyl or phenyl substituted by 3,4-methylenedioxy or from one to two substituents selected from the group consisting of hydroxy, alkoxy of 1–3 carbon atoms and halogen;
Y is selected from the group consisting of CH$_2$, CH$_2$CH$_2$, CH=CH, O and OCH$_2$;
R is alkyl of 1 to 4 carbon atoms;
and
R' is hydrogen or chlorine.

2. A compound according to claim 1 wherein R is ethyl and R' is hydrogen.

3. 4-[4-(4-Methoxybenzyl)benzyl]heptane-3,5-dione, according to claim 2.

4. 4-(4-Benzylbenzyl)heptane-3,5-dione, according to claim 2.

5. 4-[4-(4-Methoxyphenoxy)benzyl]heptane-3,5-dione, according to claim 2.

6. 4-[4-(4-Methoxyphenethyl)benzyl]heptane-3,5-dione, according to claim 2.

7. 4-[4-(4-Methoxystyryl)benzyl]heptane-3,5-dione, according to claim 2.

8. 4-[4-(4-Hydroxybenzyl)benzyl]heptane-3,5-dione, according to claim 2.

9. 4-[4-(2-Chloro-4-methylstyryl)benzyl]heptane-3,5-dione, according to claim 2.

10. 4-[4-(4-Hydroxystyryl)benzyl]heptane-3,5-dione, according to claim 2.

11. 4-[4-(2-Chloro-4-hydroxystyryl)benzyl]heptane-3,5-dione, according to claim 2.

12. 4-[4-(2-Chloro-4-methoxystyryl)-2-chlorobenzyl]-heptane-3,5-dione, according to claim 1.

13. A composition for combatting viruses which comprises an anti-virally effective amount of at least one compound according to claim 1 in admixture with a suitable carrier or diluent.

14. A method for combatting viruses which comprises contacting the locus of said viruses with a composition containing an anti-virally effective amount of at least one compound according to claim 1 in admixture with a suitable carrier or diluent.

* * * * *